US010045735B2

(12) United States Patent
Cowley et al.

(10) Patent No.: US 10,045,735 B2
(45) Date of Patent: Aug. 14, 2018

(54) BIOFEEDBACK SENSORS IN A BODY AREA NETWORK

(71) Applicant: Intel Corporation, Santa Clara, CA (US)

(72) Inventors: Nicholas P. Cowley, Wroughton (GB); Ruchir Saraswat, Swindon (GB); Richard J. Goldman, Cirencester (GB)

(73) Assignee: Intel Corporation, Santa Clara, CA (US)

( * ) Notice: Subject to any disclaimer, the term of this patent is extended or adjusted under 35 U.S.C. 154(b) by 8 days.

(21) Appl. No.: 14/499,100

(22) Filed: Sep. 27, 2014

(65) Prior Publication Data

US 2016/0089075 A1 Mar. 31, 2016

(51) Int. Cl.
| | |
|---|---|
| *A61B 5/05* | (2006.01) |
| *A61B 5/00* | (2006.01) |
| *H04B 13/00* | (2006.01) |
| *G16H 40/63* | (2018.01) |
| *H04W 4/38* | (2018.01) |
| *H04W 4/80* | (2018.01) |

(Continued)

(52) U.S. Cl.
CPC ............ *A61B 5/486* (2013.01); *A61B 5/0024* (2013.01); *A61B 5/725* (2013.01); *A61B 5/742* (2013.01);
(Continued)

(58) Field of Classification Search
CPC ..... A61B 5/486; A61B 5/0531; A61B 5/0533; A61B 5/72; A61B 5/725; A61B 5/0002; A61B 5/0028; A61B 5/0022; A61B 5/0024; A61B 5/0015; A61B 5/7228; G06F 19/34; G06F 19/3406; G06F 19/3418
See application file for complete search history.

(56) References Cited

U.S. PATENT DOCUMENTS

2007/0239229 A1 10/2007 Masoud
2008/0284607 A1 11/2008 Hyoung
(Continued)

FOREIGN PATENT DOCUMENTS

| CN | 101904119 A | 12/2010 |
|---|---|---|
| TW | I405444 B | 8/2013 |
| WO | 2013/096954 A1 | 6/2013 |

OTHER PUBLICATIONS

Office Action, Search Report, and English Translation for Taiwan Patent Application No. 104127517, dated Nov. 1, 2016, 15 pages.

(Continued)

*Primary Examiner* — Devin Henson
(74) *Attorney, Agent, or Firm* — Barnes & Thornburg LLP (57) ABSTRACT

Technologies for the sensing of biofeedback signals of a user include a body area network (BAN) system comprising one or more biofeedback sensors and one or more BAN controllers. The biofeedback sensors are configured to sense BAN signals, which may include biofeedback signals and body-coupled communication (BCC) signals. To facilitate communication, the biofeedback sensors may demultiplex the sensed BAN signals into biofeedback signals and incoming BCC signals. Similarly, the biofeedback sensors may multiplex outgoing BCC signals with sensed biofeedback signals. The BAN controller may communicate in a similar manner. Additionally, the BAN controller may process incoming BCC signals and provide feedback to the user based on BCC signals received from the biofeedback sensors.

16 Claims, 5 Drawing Sheets

(51) Int. Cl.
*A61B 5/053* (2006.01)
*H04L 29/08* (2006.01)

(52) U.S. Cl.
CPC .......... *A61B 5/7405* (2013.01); *A61B 5/7455* (2013.01); *A61B 5/7475* (2013.01); *G16H 40/63* (2018.01); *H04B 13/005* (2013.01); *H04W 4/38* (2018.02); *H04W 4/80* (2018.02); *A61B 5/0002* (2013.01); *A61B 5/0015* (2013.01); *A61B 5/0022* (2013.01); *A61B 5/0028* (2013.01); *A61B 5/0531* (2013.01); *A61B 5/0533* (2013.01); *A61B 5/72* (2013.01); *A61B 5/7228* (2013.01); *A61B 2560/0475* (2013.01); *H04L 67/12* (2013.01)

(56) References Cited

U.S. PATENT DOCUMENTS

| | | | |
|---|---|---|---|
| 2009/0275283 A1* | 11/2009 | Zhuyan | A61B 5/0028 455/41.2 |
| 2010/0312071 A1* | 12/2010 | Schenk | A61B 5/0006 600/300 |
| 2011/0196451 A1 | 8/2011 | Hill | |
| 2013/0172042 A1 | 7/2013 | Kim | |
| 2013/0217979 A1* | 8/2013 | Blackadar | A61B 5/0024 600/301 |
| 2014/0247153 A1* | 9/2014 | Proud | A61B 5/002 340/870.09 |
| 2014/0300490 A1* | 10/2014 | Kotz | A61B 5/0028 340/870.3 |
| 2015/0127737 A1* | 5/2015 | Thompson | G06F 19/322 709/204 |

OTHER PUBLICATIONS

International Search Report for PCT/US15/046749, dated Nov. 25, 2015 (4 pages).

Written Opinion for PCT/US15/046749, dated Nov. 25, 2015 (7 pages).

* cited by examiner

BIOFEEDBACK SENSORS IN A BODY AREA NETWORK

BACKGROUND

Body sensors, in particular sensors that detect electrical activity, galvanic potential, skin resistance, and the like, are becoming increasingly popular in wearable applications for providing biofeedback of the wearer. Examples of biofeedback that can be sensed using body sensors include, for example, heart rate, brain activity, temperature, muscular action, emotional state, and others. Many body sensors are characterized by a conductive plate or surface that interfaces (i.e., provides contact) with the skin of the wearer of the body sensor. The contact interface is commonly referred to as either "wet" or "dry." This distinction is based primarily on whether there is a conductive medium, such as an electrically conductive gel, between the contact interface and the skin (i.e., wet), or not (i.e., dry). Additionally, dry contact interfaces may only require being in near proximity to the skin of the wearer, such as on the outside of clothing, rather than in direct contact with the wearer's skin.

In current applications, the body sensors are typically implanted into the skin of a body, directly attached to the skin of the body, or are in proximity to the skin of the body in a wearable sensor device, such as a wrist worn device. Typical attached body sensors and/or wearable sensor devices may be linked to a main controller device by wires or other hardware interconnects. The main controller device may itself be a wearable device. However, under certain conditions, it may be inconvenient or even infeasible to run wires from each body sensor of the wearer to the main controller device.

To address such conditions, some wearable sensor devices are linked to the main controller device by some form of wireless communication, such as Bluetooth, ZigBee, and Wi-Fi. However, those forms of wireless communication are undesirable and potentially limiting in application. For example, while wireless communication offers flexibility in application, wireless communication presents interoperability concerns across the various wireless communication standards and protocols, and poses a potential security concern by exposing the data and access to the wearable sensor device to potentially harmful third parties. Additionally, wireless communications are susceptible to interference and potentially unreliable wireless networks.

BRIEF DESCRIPTION OF THE DRAWINGS

The concepts described herein are illustrated by way of example and not by way of limitation in the accompanying figures. For simplicity and clarity of illustration, elements illustrated in the figures are not necessarily drawn to scale. Where considered appropriate, reference labels have been repeated among the figures to indicate corresponding or analogous elements.

DETAILED DESCRIPTION OF THE DRAWINGS

While the concepts of the present disclosure are susceptible to various modifications and alternative forms, specific embodiments thereof have been shown by way of example in the drawings and will be described herein in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. Additionally, it should be appreciated that items included in a list in the form of "at least one of A, B, and C" can mean (A); (B); (C); (A and B); (A and C); (B and C); or (A, B, and C). Similarly, items listed in the form of "at least one of A, B, or C" can mean (A); (B); (C); (A and B); (A and C); (B and C); or (A, B, and C).

The disclosed embodiments may be implemented, in some cases, in hardware, firmware, software, or any combination thereof. The disclosed embodiments may also be implemented as instructions carried by or stored on one or more transitory or non-transitory machine-readable (e.g., computer-readable) storage media, which may be read and executed by one or more processors. A machine-readable storage medium may be embodied as any storage device, mechanism, or other physical structure for storing or transmitting information in a form readable by a machine (e.g., a volatile or non-volatile memory, a media disc, or other media device).

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features.

Figure 1:
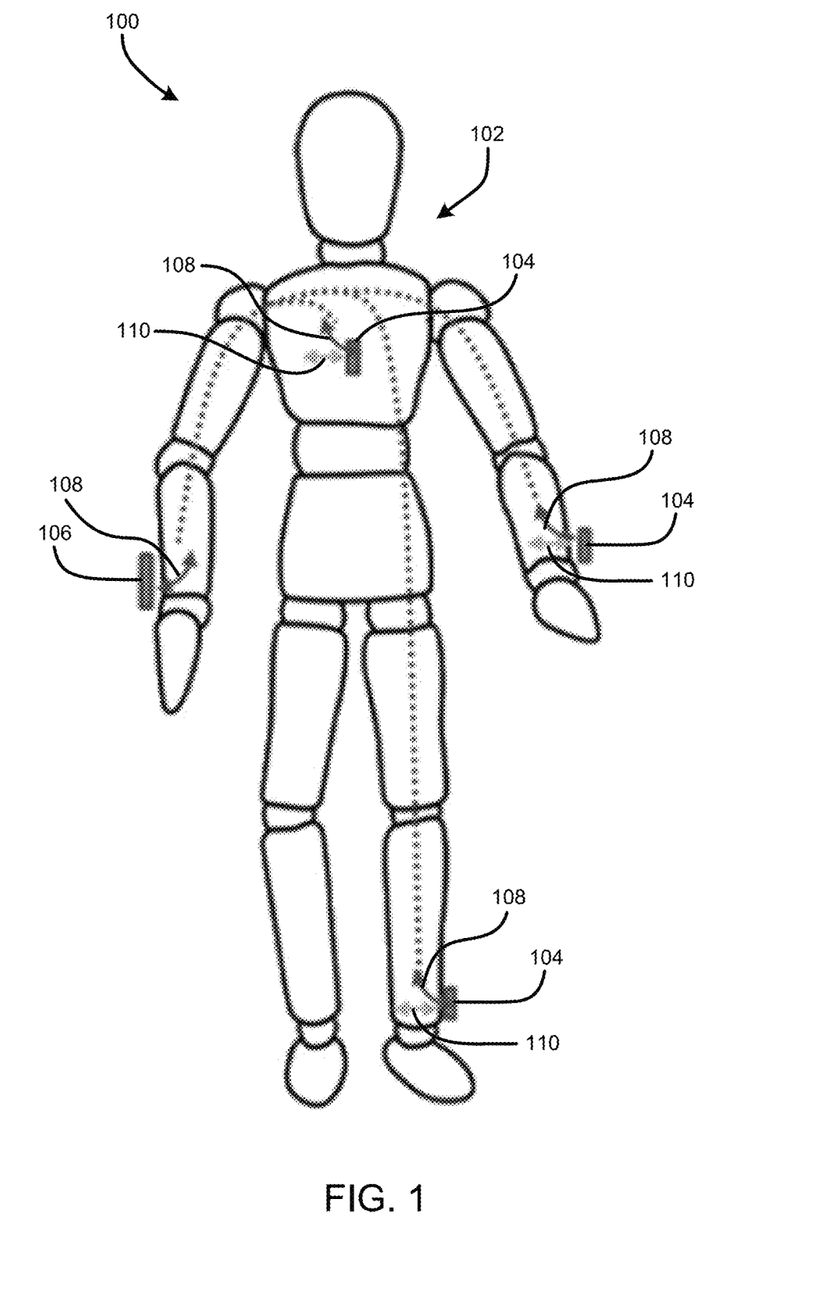
FIG. 1 is an illustration of an embodiment of a body area network (BAN) including biofeedback devices in body-coupled communication (BCC) with a BAN controller.

Referring now to FIG. 1, an illustrative embodiment of a body area network (BAN) system 100 includes one or more biofeedback sensors 104 coupled to a user 102 and a BAN controller 106, which may be worn or otherwise carried by the user 102. In use, as discussed in more detail below, the biofeedback sensors 104 and the BAN controller 106 communicate with each other through the use of electrostatic signals transmitted and received through conductive tissues in the body of the user 102, commonly referred to as body-coupled communication (BCC). In the BAN system 100, the biofeedback sensors 104 may be in direct and/or indirect contact with the body of the user 102 to detect a body area network signal (BAN signal) via an associated local sensor of the biofeedback sensors 104. Similarly, the BAN controller 106 is in direct and/or indirect contact with the body of the user 102 to communicate with the biofeedback sensors 104 via the BAN signal. As discussed in more detail below, the sensed BAN signals include a biofeedback signal 110 component and a BCC signal 108 component. The BCC signal 108 is used to provide communications between the biofeedback sensors 104 and the BAN controller 106.

Each of the biofeedback sensors 104 are configured to sense a biofeedback signal 110, such as an electrical activity signal of an organ of the body of the user 102, included in the BAN signal and transmit sensor data generated based on the sensed biofeedback signal 110 to the BAN controller 106 using a corresponding BCC signal 108. Similarly, the BAN controller 106 is configured to transmit signals (e.g., command signals) to and receive signals (e.g., communication signals including sensor data) from the biofeedback sensors 104 via a corresponding BCC signal 108. Again, it should be appreciated that the BCC signal 108 and the biofeedback signal 110 together form a BAN signal, which is initially sensed by the biofeedback sensors 104 and the BAN controller 106. As discussed in more detail below, most relevant biofeedback signals 110 generated by the user's body are embodied as low frequency signals. As such, the biofeedback sensors 104 and the BAN controller 106 communicate with each other using BCC signals 108 transmitted at frequencies higher than that of the typical biofeedback signals 110 to avoid signal interference. To receive a body-coupled communication in this manner, the biofeedback sensors 104 and BAN controller 106 are configured to demultiplex the sensed BAN signals into the individual biofeedback signal 110 and a received BCC signal 108 (if available). Similarly, to transmit a body-coupled communication, the biofeedback sensors 104 and the BAN controller 106 are configured to multiplex a transmitted BCC signal 108 with any sensed biofeedback signal 110. In this way, the biofeedback sensors 104 and the BAN controller 106 may communicate with each other via the BCC signals 108, while continuing to monitor or sense biofeedback signals 110.

Figure 2:
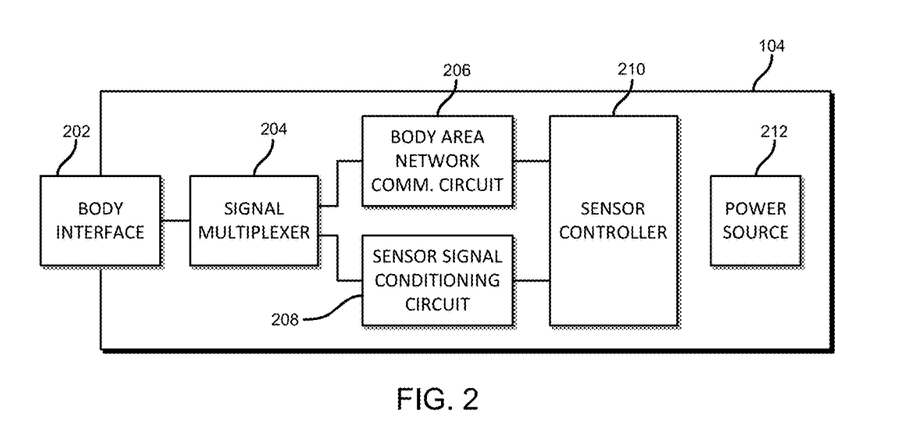
FIG. 2 is a simplified block diagram of at least one embodiment of a biofeedback device of FIG. 1.

Referring now to FIG. 2, in an illustrative embodiment, a biofeedback sensor 104 of the system 100 includes a body interface 202, a signal multiplexer 204, a body area network communication circuit 206, a sensor signal conditioning circuit 208, and a sensor controller 210. Of course, the biofeedback sensors 104 may include additional or other components in other embodiments, including those components found in a typical biofeedback sensor. The body interface 202 may be embodied as any type of interface capable of facilitating the transmission or reception of a BCC signal via the body of the user 102. For example, the body interface 202 may be embodied as a conductive plate (e.g., metallic plate), probe, wires, or other connection capable of communicatively coupling the biofeedback sensor 104 to the body of the user 102. In some embodiments, the body interface 202 may be in direct contact with skin of the body of the user 102, or in direct contact with a conductive medium applied to the skin of the body of the user 102 (i.e., a wet contact interface), such as an electrically conductive gel. In other embodiments, the body interface 202 may be in indirect contact with the skin of the body of the user 102 (e.g., through a clothing of the user 102), such as in a wearable device application. In such embodiments, the biofeedback sensor 104 may include a strap or other devices to secure the wearable device to the body of the user 102. It should be appreciated that, in some embodiments, the body interface 202 may be embodied as multiple interface devices (e.g., multiple conductive plates) depending on the type of biofeedback signals being measured or other criteria (e.g., in those applications in which a galvanic skin response is measured).

The signal multiplexer 204 may be embodied as any type of signal multiplexer capable of multiplexing and/or demultiplexing (e.g., filtering) multiple frequency ranges. In the illustrative embodiment, the signal multiplexer 204 is embodied as a bi-directional diplexer having an input coupled with the body interface 202 to receive and transmit BAN signals. The illustrative bi-directional diplexer also has two outputs—one at which the BCC signal 108 is passed (received or transmitted) and another at which the biofeedback signal 110 is passed (received biofeedback signals 110 or transmitted biofeedback stimulus signals). That is, the signal multiplexer 204 is configured to demultiplex a sensed BAN signal into an incoming BCC signal 108 (if available) and the biofeedback signal 110. Additionally, the signal multiplexer 204 is configured to multiplex any outgoing BCC signals 108 (e.g., a BCC signal transmitted from the biofeedback sensor 104 to the BAN controller 106) with any sensed biofeedback signal 110. It should be appreciated that, in the illustrative embodiment, a received biofeedback signal 110 can be passed through the signal multiplexer 204 on one path and an outgoing BCC signal 108 can be passed through the signal multiplexer 204 on another path. As discussed above, the BCC signal 108 and the biofeedback signal 110 can coexist on the same port without interference due to a difference in frequencies. As such, the illustrative signal multiplexer 204 allows for sensor data to be collected in real time by the biofeedback sensors 104 while maintaining body-coupled communication with the BAN controller 106 for monitoring of the sensor data by the user 102.

In the illustrative embodiment, the biofeedback signal output of the signal multiplexer 204 has a low pass filtering characteristic, passing BAN signals below an upper threshold frequency (e.g., signals below about 150 Hz). Additionally, in the illustrative embodiment, the BCC signal output of the signal multiplexer 204 has a high pass filtering characteristic, passing BAN signals above a lower threshold frequency (e.g., signals above 1 MHz). In some embodiments, the BCC signal output of the signal multiplexer 204 may have a band pass filtering characteristic, passing BAN signals between a lower threshold frequency and an upper threshold frequency. For example, in an illustrative embodiment, the BCC signal output passes BAN signals between 1 MHz and 100 MHz, which is a beneficial frequency range to pass data carrying signals through the body of a human user 102 as discussed in more detail below in regard to FIGS. 5 and 6. In some embodiments, the signal multiplexer 204 may be embodied as, or otherwise include, one or more discrete filters, including low pass filters, high pass filters, band pass filters, or the like. Additionally or alternatively, in some embodiments, the signal multiplexer 204 may include a signal attenuator or other electrical devices or circuits useful in separating the sensed BAN signal into the BCC signal 108 and the biofeedback signal 110.

In the illustrative embodiment, the BCC signal output of the signal multiplexer 204 is coupled to the BAN communication circuit 206, and the biofeedback signal output of the signal multiplexer 204 is coupled to the sensor signal conditioning circuit 208. The BAN communication circuit 206 may be embodied as any type of communication circuit capable of enabling communications between the biofeedback sensors 104 and the BAN controller 106 using body-coupled communication. In an illustrative embodiment, the BAN communication circuit 206 is embodied as a physical layer bidirectional transceiver for transmitting a BCC signal 108 including sensor data (i.e., a communication signal) to and receiving a BCC signal 108 from the BAN controller 106 and/or other biofeedback sensors 104.

The sensor signal conditioning circuit 208 may be embodied as any type of sensor circuit capable of conditioning, or otherwise sensing, the biofeedback signal 110. For example, in the illustrative embodiment, the sensor signal conditioning circuit 208 is embodied as a physical layer sensor circuit configured to pre-process the biofeedback signal 110 to prepare the biofeedback signal 110 for further processing or analysis by the sensor controller 210. To do so, the sensor signal conditioning circuit 208 may include any number of signal conditioning or other sensor devices or sub-circuits including, but not limited to a transimpedance amplifier, a variable gain amplifier, one or more filters, and/or other signal condition components. In some embodiments, depending on the type of sensor, the sensor signal conditioning circuit 208 may be unidirectional or bidirectional. It should be appreciated that the sensor signal conditioning circuit 208 may form a specialized sensor circuit including, but not limited to, an electrical activity level sensor, a galvanic potential sensor, and/or a skin resistance sensor. Additionally, it should be appreciated that, in some embodiments, the biofeedback sensor 104 may include more than one sensor signal conditioning circuit 208 to facilitate the sensing of different types of biofeedback signals 110.

In the illustrative embodiment, each of the BAN communication circuit 206 and the sensor signal conditioning circuit 208 are coupled to the sensor controller 210. The sensor controller 210 may be embodied as any type of controller or control circuit capable of generating sensor data based on the biofeedback signal 110 and controlling the BAN communication circuit 206 to transmit the sensor data to the BAN controller 106. For example, the sensor controller 210 may be embodied as a single or multi-core processor(s), digital signal processor, microcontroller, or other processor or processing/controlling circuit. In an illustrative embodiment, the sensor controller 210 is embodied as a media access controller (MAC) capable of controlling and processing the BCC signal 108 and the biofeedback signal 110. The sensor controller 210 is further capable of responding to BCC signals 108 (e.g., command signals) received from the BAN controller 106. For example, if the sensor controller 210 receives a BCC signal 108 from the BAN controller 106 that includes an interrogation command (as discussed below), the sensor controller 210 may be configured to respond to such commands (e.g., by transmitting sensor data or taking some other action).

In the illustrative embodiment, each of the biofeedback sensors 104 includes a local power source 212 to supply power to the various components of each biofeedback sensor 104. In an illustrative embodiment, the power source 212 is embodied as a battery, though it should be appreciated that the power source 212 may be embodied as any type of power supplying source capable of supplying power to each of the biofeedback sensors 104 in other embodiments. Additionally, in some embodiments, the power source 212 may be embodied as a rechargeable power source.

Figure 3:
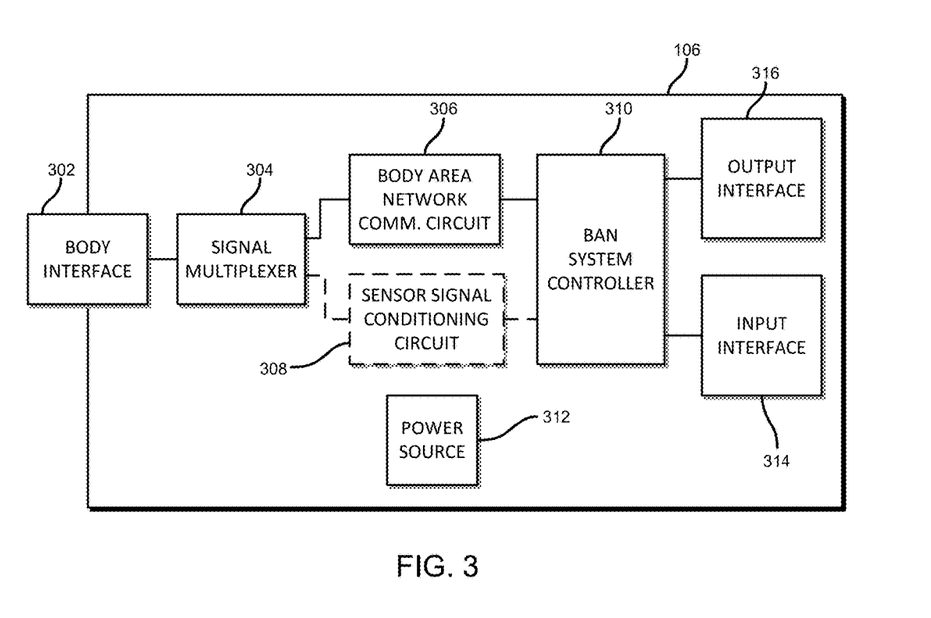
FIG. 3 is a simplified block diagram of at least one embodiment of the BAN controller device of FIG. 1.

Referring now to FIG. 3, in an illustrative embodiment, the BAN controller 106 includes a body interface 302, a signal multiplexer 304, a BAN communication circuit 306, and a power source 312, each of which is configured similarly to, and functions in a manner similar to, the corresponding components of the biofeedback sensor 104 of FIG. 2. For example, as described above in regard to the signal multiplexer 204, the signal multiplexer 304 may be embodied as a bi-directional diplexer in illustrative embodiments. Further description of those components of the BAN controller 106 is not repeated herein for clarity of the description with the understanding that the description of the corresponding components provided above in regard to FIG. 2 apply equally to the corresponding components of the BAN controller 106. In some embodiments, the BAN controller 106 may additionally be configured to function as a sensor, and, as such, include a sensor signal conditioning circuit 308, which functions similarly as the sensor signal conditioning circuit 208 of the biofeedback sensor 104 of FIG. 2.

In the illustrative embodiment, the BAN controller 106 also includes a BAN system controller 310 coupled to the BAN communication circuit 306 and, if applicable, the sensor signal conditioning circuit 308. The BAN system controller 310 may be embodied as any type of controller configured to interpret the communication signal (i.e., the BCC signal 108 including sensor data) received from the biofeedback device(s) 106 and generate output data based on the communication signal. For example, the BAN system controller 310 may be embodied as a single or multi-core processor(s), digital signal processor, microcontroller, or other processor or processing/controlling circuit.

In some embodiments, the BAN system controller 310 is additionally coupled to one or more input interfaces 314 and/or output interfaces 316. Each of the input interfaces 314 may be embodied as any type of human-machine interface (HMI) capable of receiving input from the user 102. For example, the input interface 314 may be embodied as one or more physical or virtual buttons, a keypad, dial, or other input device. Additionally, in some embodiments, the input interface 314 may be embodied as, or otherwise include, a microphone capable of interpreting and processing speech of the user 102 into instructions to facilitate hands-free operation of the BAN controller 106.

Each of the output interfaces 316 may be embodied as any type of output device capable of providing feedback to the user 102 based on the output data generated by the BAN system controller 310. For example, the output interface 316 may be embodied as a visual, audible, or tactile output device. In an illustrative embodiment, the output interface 316 includes a display configured to provide a visual feedback and/or a speaker to provide an audible feedback. The display may be embodied as any type of display capable of displaying digital information such as a liquid crystal display (LCD), a light emitting diode (LED), a plasma display, a cathode ray tube (CRT), or other type of display device. In some embodiments, the input interface 314 may be coupled to, or otherwise embedded with, the output interface 316. For example the display may be coupled to a touch screen to allow the user 102 to interact with the BAN system controller 310.

In some embodiments, the BAN system controller 310 may be connected to one or more external actuators and configured to take an action (e.g., based on sensor data) on an externally and/or internally attached device configured to receive and interpret an actuator command from the BAN system controller 310. For example, the BAN system controller 310 may be coupled to an actuator of an insulin pump to control the delivery of insulin to the user 102 or other medical device.

In some embodiments, the BAN controller 106 may include additional and/or alternative features or components. Such additional components may include, but are not limited to, an accelerometer and/or a gyroscope for determining additional and/or alternative feedback. Further, the BAN controller 106 and/or the biofeedback sensors 104 may include additional and/or alternative components not shown in FIGS. 2 and 3 to preserve clarity of the description including, but not limited to, data storage devices, memory, communication circuitry, I/O systems, and/or the like. In some embodiments, the biofeedback sensors 104 may additionally include input and output interfaces, similar to the BAN controller 106, for receiving input from the user 102 and outputting sensor feedback to the user 102, respectively.

Figure 4:
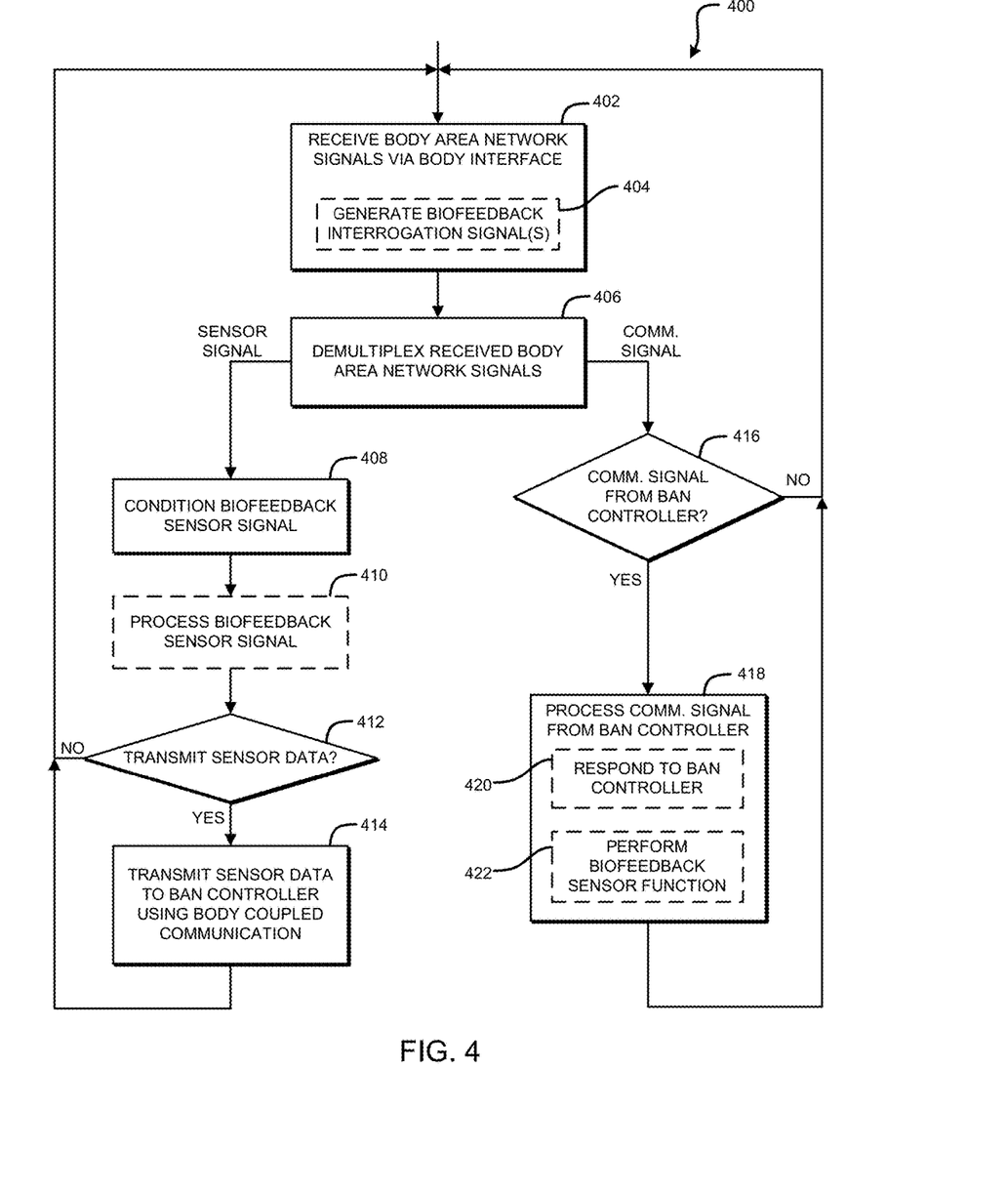
FIG. 4 is a simplified flow diagram of at least one embodiment of a method for biofeedback device communication via the BAN of FIG. 1.

Referring now to FIG. 4, in use, each biofeedback sensor 104 may execute a method 400 for receiving and demultiplexing the sensed BAN signal into the BCC signal 108 and the biofeedback signal 110. The method 400 begins in block 402, in which the biofeedback sensor 104 senses or detects a BAN signal via the body interface 202. As discussed above, the BAN signal includes the biofeedback signal 110 generated naturally by the body of the user 102 and may also include a BCC signal 108 generated by the BAN controller 106 (or other biofeedback sensor 104). Depending on the type of biofeedback sensor 104 (e.g., the type of sensor signal conditioning circuit 208), the biofeedback sensor 104 may be configured to sense or detect any type of biofeedback signal 110 from the BAN signal. For example, in some embodiments, the biofeedback sensor 104 may be configured to generate a biofeedback interrogation signal in block 404, which is applied to the body of the user 102 via the body interface 202, to properly sense or detect the desired biofeedback signal 110. The biofeedback interrogation signal may be embodied as, for example, a voltage or other bioelectrical signal used to measure a biofeedback characteristic (e.g., galvanic response) of the user 102. To facilitate continued communication, the biofeedback interrogation signal may be multiplexed with any incoming and/or outgoing BCC signals 108 via the bi-directional signal multiplexer 204.

If a BAN signal is sensed or received in block 402, the method 400 advances to block 406. In block 406, the signal multiplexer 204 of the biofeedback sensor 104 demultiplexes the received BAN signal. For example, in the illustrative embodiment in which the signal multiplexer 204 is embodied as a diplexer, the signal multiplexer 204 demultiplexes the BAN signal into two outputs. One of the outputs is embodied as the biofeedback signal 110 and is handled via the method flow of blocks 408-414 discussed below, and the other output is embodied as the BCC signal 108 and is handled via the method flow of block 416-422.

In block 408, the sensor signal conditioning circuit 208 conditions the biofeedback sensor signal. Based on the type of biofeedback signal 110 being monitored and/or the type of biofeedback sensor 104, the sensor signal conditioning circuit 208 may perform any useful conditioning on the biofeedback signal 110. For example, the biofeedback signal 110 may be amplified, filtered, quantized, converted, or otherwise adapted in block 408 by the sensor signaling conditioning circuit 208.

In some embodiments, the biofeedback sensor 104 may have some amount of processing capabilities. As such, in block 410, the sensor controller 210 may perform processing on the conditioned biofeedback signal 110. For example, the sensor controller 210 may generate sensor data indicative of, or otherwise based on, the conditioned biofeedback signal 110. Additionally, in other embodiments, the sensor controller 210 may be configured to accumulate and/or aggregate biofeedback signals over time and generate periodic or aggregate sensor data indicative of such biofeedback signals.

In block 412, the biofeedback sensor 104 determines whether to transmit sensor data of the biofeedback sensor signal. As discussed above, in some embodiments, the biofeedback sensor 104 may aggregate "chunks" of data prior to transmitting the sensor data. For example, the biofeedback sensor 104 may be configured to only transmit the sensor data at a pre-set time interval, and every sensor data (or raw biofeedback signal 110) generated or sensed between the transmission time intervals may be locally stored and aggregated until it is sent as a "chunk" in the next transmission. In other embodiments, the biofeedback sensor 104 may be configured to only transmit the sensor data once the aggregate of sensor data reaches a predetermined size. If the biofeedback sensor 104 determines not to transmit the sensor data, the method 400 loops back to block 402. If, however, the biofeedback sensor 104 determines to transmit the sensor data, the method 400 advances to block 414.

In block 414, the sensor data is transmitted to the BAN controller 106 via a BCC signal 108. To do so, the sensor controller 210 of the biofeedback sensor 104 may generate the sensor data and control the body area network communication circuit 206 to transmit the sensor data as a BCC signal 108. For example, in some embodiments, the sensor controller 210 may modulate the communication signal (i.e., the sensor data) with a carrier signal of the BCC signal 108. As discussed above, the outgoing BCC signal 108 may be multiplexed with any sensed biofeedback signal 110 (and any outgoing biofeedback interrogation signal) via the bi-directional signal multiplexer 204.

Referring back to block 406, as discussed above, the signal multiplexer 204 also produces a BCC signal 108 from the sensed BAN signal, which is handled by the method flow of blocks 416-422. In block 416, the biofeedback sensor 104 determines whether the BCC signal 108 is a communication signal transmitted from the BAN controller 106. If not, the method 400 loops back to block 402 in which the biofeedback sensor 104 continues to sense or detect BAN signals. If, however, the BCC signal 108 is a communication signal from the BAN controller 106, the method 400 advances to block 418 in which the BCC signal 108 is processed by the biofeedback sensor 104. Of course, it should be appreciated that, in some embodiments, the BCC signal 108 may be transmitted from another biofeedback sensor 104, rather than the BAN controller 106. Regardless, if a BCC signal 108 is sensed and produced by the signal multiplexer 204, the biofeedback sensor 104 may process such signal in block 418.

In the illustrative embodiment, the BCC signal 108 is received by the body area network communication circuit 206, which may perform signal conditioning and/or other communication processing (e.g., protocol stripping) on the BCC signal 108 to generate communication data. The generated communication data is passed to the sensor controller 210, which may further process the communication data. Depending on the type of communication data, the sensor controller 210 may perform particular actions. For example, in block 420, the communications data may prompt the biofeedback sensor 104 to respond to the BAN controller 106 (e.g., by sending a "chunk" of aggregated or stored sensor data). Additionally or alternatively, the biofeedback sensor 104 may perform various sensor functions, such as adjusting sensor sensitivity, varying the particular biofeedback signals monitored, adjusting reporting windows and/or amount of sensor data reported, and/or other functions related to the operation of the biofeedback sensor 104. Regardless, after the BCC signal 108 has been processed in block 418, the method 400 loops back to block 402 in which the biofeedback sensor 104 continues sensing or detecting BAN signals.

Figure 5:
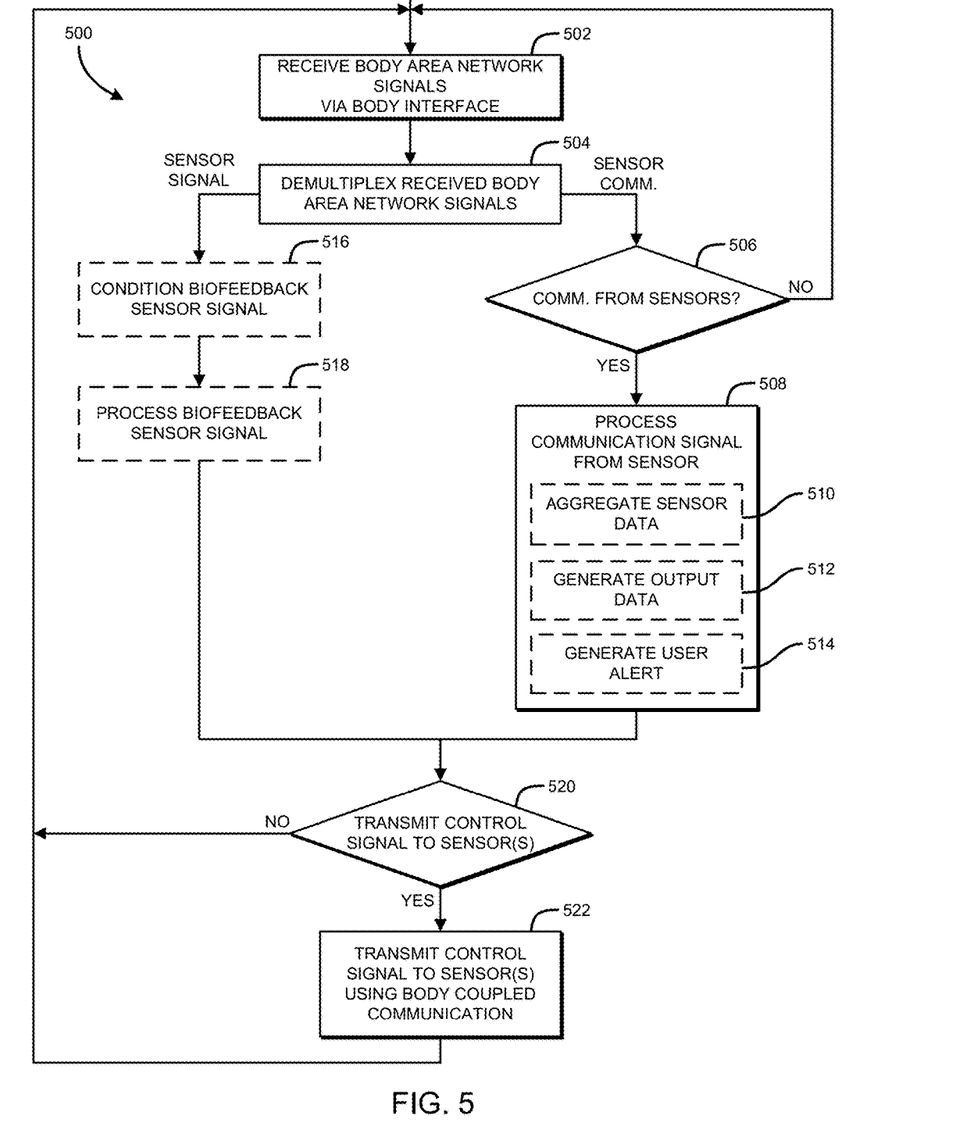
FIG. 5 is a simplified flow diagram of at least one embodiment of a method for BAN controller communication via the BAN of FIG. 1.

Referring now to FIG. 5, in use, the BAN controller 106 may execute a method 500 for receiving and demultiplexing the sensed BAN signal into the BCC signal 108. The method 500 begins with block 502, in which the BAN controller 106 receives a BAN signal via the body interface 302. If a BAN signal is sensed or received in block 502, the method 500 advances to block 504. In block 504, the signal multiplexer 304 of the BAN controller 106 demultiplexes the received BAN signal to produce the BCC signal 108. For example, as discussed above, the signal multiplexer 304 may apply a high pass filter to the received BAN signal to produce the BCC signal 108. Alternatively, in some embodiments, the signal multiplexer 304 applies a band pass filter to the received BAN signal to produce the BCC signal 108. In such embodiments, the signal multiplexer 304 passes only that range of frequencies corresponding to the band pass frequency range (e.g., between 1 MHz and 100 MHz). Regardless, the filtered or produced BCC signal 108 is handled by the method flow of blocks 506-514.

In block 506, the BAN controller 106 determines whether the BCC signal 108 was generated by one of the biofeedback sensors 104. To do so, in some embodiments, a unique identifier corresponding to each of the biofeedback sensors 104 may be included in a BCC signal 108 transmitted by the corresponding biofeedback sensor 104 as discussed above. Of course, in other embodiments, the BAN controller 106 may receive communications from other devices of the BAN system 100 instead of, or in addition to, the biofeedback sensors 104.

If the BAN controller 106 determines there is no BCC signal 108 included in the sensed BAN signal, the method 500 loops back to block 502. If, however, the BAN controller 106 determines there is a BCC signal 108, the method advances to block 508 in which the BAN controller 106 processes the BCC signal 108. To do so, the BCC signal 108 is received by the BAN communication circuit 306, which may perform signal conditioning and/or other communication processing (e.g., protocol stripping) on the BCC signal 108 to generate communication data. The generated communication data is passed to the BAN system controller 310 of the BAN controller 106, which may further process the communication data. For example, in block 510, the BAN controller 106 may be configured to aggregate sensor data received from one or more biofeedback sensors 104. In some embodiments, the aggregated data may be stored in a local memory of the BAN controller 106. Additionally, in some embodiments, the BAN controller 106 may generate an output in block 512. For example, the BAN controller 106 may display the sensor data in real-time or near real-time for monitoring by the user 102, display graphics or other indicia of the sensor data, and/or generate other output on one or more of the output interfaces 316. Further, in some embodiments, in block 514, the BAN controller 106 may process sensor data and generate an alert to the user 102 based on the sensor data. For example, the BAN controller 106 may generate an alert if the sensor data is outside an expected range (e.g., a detected heart rate is greater than an alert threshold for heart rate). The BAN controller 106 may generate any type of alert including, for example, an audible, visual, or tactile alert. In some embodiments, the behavior of the BAN controller 106, generally, and the BAN system controller 310, specifically, may be influenced by the user 102 via the input interface 314.

As discussed above, the BAN controller 106 may include biofeedback sensing capabilities in some embodiments. In such embodiments, the signal multiplexer 304 may further produce a biofeedback signal 110, which is handled via the method flow of blocks 516 and 518. In block 516, sensor signal conditioning circuit 308 conditions the biofeedback signal 110. Again, based on the type of biofeedback signal 110 being monitored and/or the type of biofeedback sensor 104, the sensor signal conditioning circuit 308 may perform any useful conditioning on the biofeedback signal 110. For example, the biofeedback signal 110 may be amplified, filtered, quantized, converted, or otherwise adapted in block 408 by the sensor signal conditioning circuit 308.

Similar to the biofeedback sensor 104, the BAN controller 106 may perform processing on the conditioned biofeedback signal 110 in block 518. For example, the BAN controller 106 may generate sensor data indicative of, or otherwise based on, the conditioned biofeedback signal 110. Additionally, in other embodiments, the BAN controller 106 may be configured to accumulate and/or aggregate biofeedback signals over time and generate periodic or aggregate sensor data indicative of such biofeedback signals. Further, as discussed above, the BAN controller 106 may generate output and/or alerts based on such sensor data.

After the BAN controller 106 has processed the BCC signal 108 in block 508 and/or any sensed biofeedback signal 110 in block 518, the method 500 advances to block 520 in which the BAN controller 106 determines whether any control signal or other communication should be transmitted to one or more biofeedback sensors 104. As discussed above, the BAN controller 106 may transmit control communications to the biofeedback sensors 104 to retrieve sensed data and/or control operation of the biofeedback sensors 104. If the BAN controller 106 determines to transmit control signals, the method 500 advances to block 522 in which the BAN controller 106 transmits control or other communication signals to one or more biofeedback sensors 104 using body-coupled communication. As discussed above, any such outgoing BCC signals 108 are transmitted through the signal multiplexer 304, which may multiplex the outgoing BCC signal 108 with any sensed biofeedback signal 110. It should be appreciated that the transmissions from the BAN controller 106 may be embodied as broadcast transmissions, which are received by each biofeedback sensor 104 of the BAN system 100. Alternatively, the transmissions may be embodied as directed transmission to be received by a particular biofeedback sensor 104 (e.g., via inclusion of an identifier of the desired biofeedback sensor 104).

Figure 6:
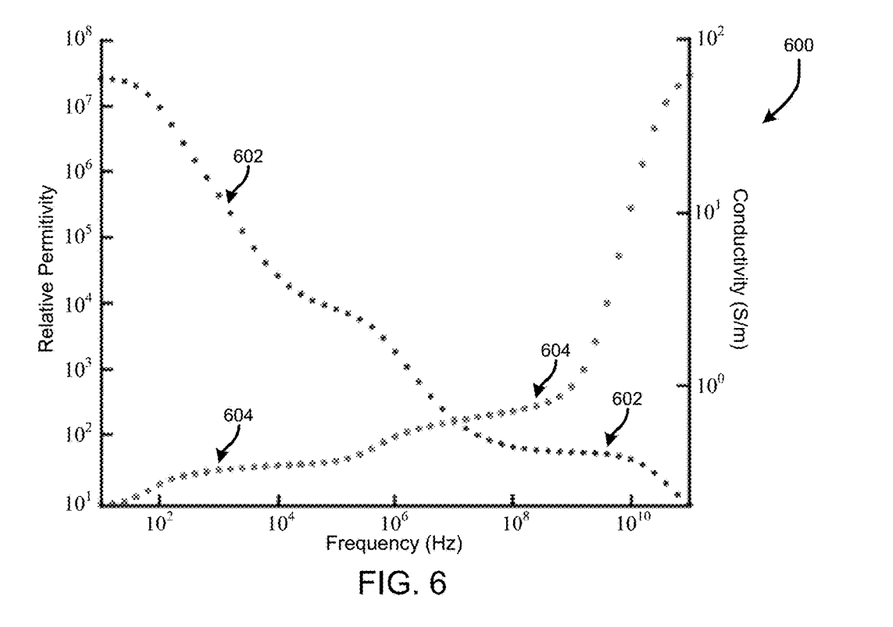
FIG. 6 is a graph illustrating the relative permittivity and conductivity of data transmission via BCC through body tissue across a series of frequency bands.

Referring now to FIG. 6, a graph 600 illustrates an idealized frequency dependence of the complex permittivity and conductivity of body tissue of a user 102 across a dielectric spectrum of biological tissue. The graph 600 includes relative permittivity data points 602 and conductivity data points 604 across an alpha dispersion in the hertz frequency range (i.e., a low frequency range), a beta dispersion in the KHz to MHz frequency range (i.e., a medium frequency range), and a gamma dispersion frequency range in excess of the MHz frequency range (i.e., a high frequency range). It should be appreciated that the graph 600 depicts the effective capability of a body of a user 102 to transmit information with a varying frequency. As shown, while the coupling impedance decreases with frequency, the effective impedance increases. As such, there is a frequency range in which the balance of conductivity and permittivity are "optimally" or desirably balanced (i.e., between a few MHz and a few 100s MHz). In the identified frequency range, the signal energy transmitted between two points on the body of a user 102 is maximized or otherwise increased.

Figure 7:
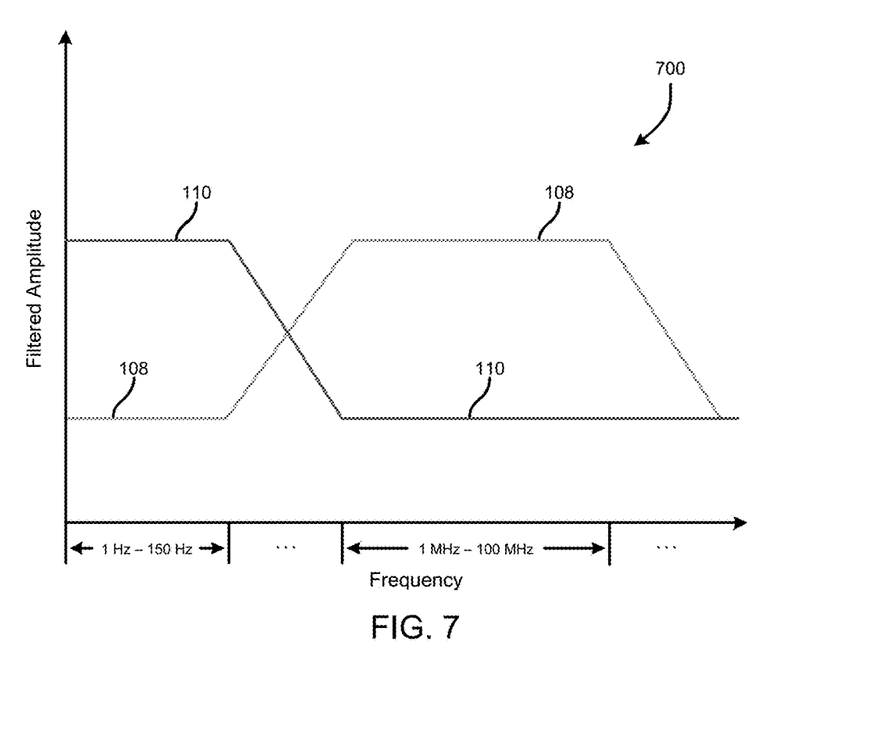
FIG. 7 is a simplified graph illustrating frequency ranges for a biofeedback signal and a BCC signal.

Referring now to FIG. 7, a simplified graph 700 illustrates an embodiment of the filtering function of the signal multiplexers 204, 304. As discussed above, the signal multiplexers 204, 304 demultiplex a sensed BAN signal into an incoming BCC signal 108 and the biofeedback signal 110 and multiplexes any outgoing BCC signals 108 with incoming biofeedback signals 110 (and/or outgoing biofeedback interrogation signals). Accordingly, as shown in FIG. 7, the biofeedback signal 110 has been filtered via a low pass filter function to be responsive in the 1 Hz to 150 Hz frequency range (i.e., a low frequency range), and the BCC signal 108 has been filtered via a band pass filter function to be responsive in the 1 MHZ to 100 MHz frequency range (i.e., a high frequency range). In this way, the two signals 108, 110 may coexist in the BAN signal with minimal interference between the individual signals 108, 110.

EXAMPLES

Illustrative examples of the technologies disclosed herein are provided below. An embodiment of the technologies may include any one or more, and any combination of, the examples described below.

Example 1 includes a biofeedback sensor for sensing biofeedback signals of a user, the biofeedback sensor comprising a body interface to receive body area network signals; a signal multiplexer having an input coupled to the body interface to receive the body area network signals, a first output, and a second output, the signal multiplexer to demultiplex the body area network signals to produce a biofeedback signal at the first output and a body-coupled communication signal at the second output; and a sensor signal conditioning circuit coupled to the first output of the signal multiplexer, the sensor signal conditioning circuit to process the biofeedback signal; and a body area network communication circuit coupled to the second output of the signal multiplexer, the body area network communication circuit to process the body-coupled communication signal.

Example 2 includes the subject matter of Example 1, and wherein the body area network communication circuit is further to transmit an outgoing body-coupled communication signal, and the signal multiplexer comprises a bi-directional signal multiplexer to multiplex the outgoing body-coupled communication signal with the biofeedback signal.

Example 3 includes the subject matter of any of Examples 1 and 2, and further including a sensor controller to generate sensor data based on the biofeedback signal and control the body area network communication circuit to transmit the sensor data to a body area network controller via body-coupled communication.

Example 4 includes the subject matter of any of Examples 1-3, and wherein the sensor data includes a unique identifier corresponding to the biofeedback sensor.

Example 5 includes the subject matter of any of Examples 1-4, and wherein the sensor controller comprises a media access controller.

Example 6 includes the subject matter of any of Examples 1-5, and wherein the body interface comprises a conductive metallic plate.

Example 7 includes the subject matter of any of Examples 1-6, and wherein the body interface is in direct contact with at least one of a body of the user or a conductive medium.

Example 8 includes the subject matter of any of Examples 1-7, and wherein the body interface is in indirect contact with the body.

Example 9 includes the subject matter of any of Examples 1-8, and wherein the signal multiplexer comprises a diplexer.

Example 10 includes the subject matter of any of Examples 1-9, and wherein the signal multiplexer includes at least one of a low pass filter or a high pass filter.

Example 11 includes the subject matter of any of Examples 1-10, and wherein the biofeedback signal comprises at least one of an electrical activity level, a galvanic potential, or a skin resistance.

Example 12 includes the subject matter of any of Examples 1-11, and wherein the biofeedback signal is in a low frequency range and the body-coupled communication signal is in a high frequency range that is higher than the low frequency range.

Example 13 includes the subject matter of any of Examples 1-12, and wherein the low frequency range is from 1 Hz to 150 Hz and the high frequency range is from 1 MHz to 100 MHz.

Example 14 includes the subject matter of any of Examples 1-13, and wherein the sensor signal conditioning circuit includes at least one of a transimpedance amplifier, a variable gain amplifier, or a filter.

Example 15 includes the subject matter of any of Examples 1-14, and wherein the sensor signal conditioning circuit includes at least one of a receiver, a transmitter, or a transceiver.

Example 16 includes the subject matter of any of Examples 1-15, and wherein the body area network communication circuit includes at least one of a receiver, a transmitter, or a transceiver.

Example 17 includes the subject matter of any of Examples 1-16, and further including a power source to provide power to the biofeedback sensor.

Example 18 includes a body area network controller for controlling a body area network comprising one or more biofeedback sensors, the body area network controller comprising a body interface to receive body area network signals; a signal multiplexer having an input coupled to the body interface to receive the body area network signals, the signal multiplexer to demultiplex the body area network signals to produce a body-coupled communication signal, wherein the body-coupled communication signal comprises a communication signal transmitted by one of the biofeedback sensors by body-coupled communication; a body area network communication circuit coupled to the signal multiplexer, the body area network communication circuit to process the communication signal; and a body area network system controller coupled to the body area network communication circuit to generate output data based on the communication signal.

Example 19 includes the subject matter of Example 18, and further including a sensor signal conditioning circuit coupled to the signal multiplexer, wherein the signal multiplexer is further to demultiplex the body area network signals to produce a biofeedback signal, wherein the sensor signal continuation circuit is to process the biofeedback signal, and wherein the body area network system controller is further coupled to the sensor signal conditioning circuit to generate sensor data based on the biofeedback signal.

Example 20 includes the subject matter of any of Examples 18 and 19, and wherein the body area network communication circuit is further to transmit an outgoing body-coupled communication signal, and the signal multiplexer comprises a bi-directional signal multiplexer to multiplex the outgoing body-coupled communication signal with the biofeedback signal.

Example 21 includes the subject matter of any of Examples 18-20, and wherein the biofeedback signal comprises at least one of an electrical activity level, a galvanic potential, or a skin resistance.

Example 22 includes the subject matter of any of Examples 18-21, and wherein the biofeedback signal is in a low frequency range and the body-coupled communication signal is in a high frequency range that is higher than the low frequency range.

Example 23 includes the subject matter of any of Examples 18-22, and wherein the low frequency range is from 1 Hz to 150 Hz and the high frequency range is from 1 MHz to 100 MHz.

Example 24 includes the subject matter of any of Examples 18-23, and wherein the sensor signal conditioning circuit includes at least one of a transimpedance amplifier, a variable gain amplifier, or a filter.

Example 25 includes the subject matter of any of Examples 18-24, and wherein the sensor signal conditioning circuit includes at least one of a receiver, a transmitter, or a transceiver.

Example 26 includes the subject matter of any of Examples 18-25, and further including an output interface to provide feedback to a user of the body area network controller based on the output data.

Example 27 includes the subject matter of any of Examples 18-26, and wherein the feedback to the user includes at least one of a visual feedback, an audible feedback, or a tactile feedback.

Example 28 includes the subject matter of any of Examples 18-27, and further including an input interface to receive an input command from a user of the body area network controller to control one or more of the biofeedback sensors.

Example 29 includes the subject matter of any of Examples 18-28, and wherein the input command includes at least one of an interrogation command to request sensor data from one or more of the biofeedback sensors or a calibration command to instruct at least one of the biofeedback sensors to calibrate.

Example 30 includes the subject matter of any of Examples 18-29, and wherein the body interface comprises a conductive metallic plate.

Example 31 includes the subject matter of any of Examples 18-30, and wherein the body interface is in direct contact with at least one of a body of the user and a conductive medium.

Example 32 includes the subject matter of any of Examples 18-31, and wherein the body interface is in indirect contact with the body.

Example 33 includes the subject matter of any of Examples 18-32, and wherein the body area network communication circuit includes at least one of a receiver, a transmitter, or a transceiver.

Example 34 includes the subject matter of any of Examples 18-33, and wherein the communication signal includes sensor data corresponding to a biofeedback signal sensed by a biofeedback sensor.

Example 35 includes the subject matter of any of Examples 18-34, and wherein the communication signal further includes a biofeedback sensor identifier corresponding to a biofeedback sensor that transmitted the body-coupled communication signal.

Example 36 includes the subject matter of any of Examples 18-35, and wherein the body area network system controller comprises a media access controller.

Example 37 includes the subject matter of any of Examples 18-36, and wherein the signal multiplexer comprises a diplexer.

Example 38 includes the subject matter of any of Examples 18-37, and wherein the signal multiplexer includes at least one of a low pass filter or a high pass filter.

Example 39 includes the subject matter of any of Examples 18-38, and further including at least one of an accelerometer or a gyroscope.

Example 40 includes the subject matter of any of Examples 18-39, and wherein the body area network system controller is further communicatively coupled to one or more external actuators.

Example 41 includes a method for sensing body area network signals of a user, the method comprising receiving, by a body interface of a biofeedback sensor, body area network signals of the user; demultiplexing, by a signal multiplexer of the biofeedback sensor, the body area network signals to produce a biofeedback signal and a body-coupled communication signal; processing, by a sensor signal conditioning circuit of the biofeedback sensor, the biofeedback signal; and processing, by a body area network communication circuit, the body-coupled communication signal.

Example 42 includes the subject matter of Example 41, and further including transmitting, by the body area network communication circuit, an outgoing body-coupled communication signal; and multiplexing, by the signal multiplexer, the outgoing body-coupled communication signal with the biofeedback signal.

Example 43 includes the subject matter of any of Examples 41 and 42, and further including generating, by a sensor controller, sensor data based on the biofeedback signal; and controlling, by the sensor controller, the body area network communication circuit to transmit the sensor data to a body area network controller by body-coupled communication.

Example 44 includes the subject matter of any of Examples 41-43, and wherein generating the sensor data is further based on a unique identifier corresponding to the biofeedback sensor.

Example 45 includes the subject matter of any of Examples 41-44, and wherein generating the sensor data based on the biofeedback signal comprises generating, by a media access controller, sensor data based on the biofeedback signal.

Example 46 includes the subject matter of any of Examples 41-45, and wherein receiving the body area network signals by the body interface comprises receiving the body area network signals by a conductive metallic plate.

Example 47 includes the subject matter of any of Examples 41-46, and wherein receiving the body area network signals by the body interface comprises receiving the body area network signals by a body interface in direct contact with at least one of a body of the user or a conductive medium.

Example 48 includes the subject matter of any of Examples 41-47, and wherein receiving the body area network signals by the body interface comprises receiving the body area network signals by a body interface in indirect contact with the body.

Example 49 includes the subject matter of any of Examples 41-48, and wherein demultiplexing the body area network signals by a signal multiplexer of the biofeedback sensor comprises demultiplexing the body area network signals by a diplexer.

Example 50 includes the subject matter of any of Examples 41-49, and wherein demultiplexing the body area network signals by the signal multiplexer comprises demultiplexing the body area network signals by at least one of a low pass filter or a high pass filter.

Example 51 includes the subject matter of any of Examples 41-50, and wherein receiving the body area network signals of the user includes receiving at least one of an electrical activity level, a galvanic potential, or a skin resistance.

Example 52 includes the subject matter of any of Examples 41-51, and wherein demultiplexing the body area network signals comprises demultiplexing the body the biofeedback signals to produce a biofeedback signal in a low frequency range and a body-coupled communications signal in a high frequency range that is higher than the low frequency range.

Example 53 includes the subject matter of any of Examples 41-52, and wherein the low frequency range is from 1 Hz to 150 Hz and the high frequency range is from 1 MHz to 100 MHz.

Example 54 includes the subject matter of any of Examples 41-53, and wherein processing the biofeedback signal by the sensor signal conditioning circuit comprises processing the biofeedback signal by at least one of a transimpedance amplifier, a variable gain amplifier, or a filter.

Example 55 includes a method for controlling a body area network comprising one or more biofeedback sensors, the method comprising receiving, by a body interface of a body area network controller, body area network signals of the user; demultiplexing, by a signal multiplexer of the body area network controller, the body area network signals to produce a body-coupled communication signal, the body-coupled communication signal comprising a communication signal transmitted by one of the biofeedback sensors using body-coupled communication; processing, by a body area network communication circuit, the communication signal; and generating, by a body area network system controller of the body area network controller, output data based on the communication signal.

Example 56 includes the subject matter of Example 55, and further including demultiplexing, by the signal multiplexer of the body area network controller, the body area network signals to produce a biofeedback signal; processing, by a sensor signal conditioning circuit coupled to the signal multiplexer, the biofeedback signal; and generating, by the body area network system controller, sensor data based on the biofeedback signal.

Example 57 includes the subject matter of any of Examples 55 and 56, and further including transmitting, by the body area network communication circuit, an outgoing body-coupled communication signal; and multiplexing, by the signal multiplexer, the outgoing body-coupled communication signal with the biofeedback signal.

Example 58 includes the subject matter of any of Examples 55-57, and wherein receiving the body area network signals of the user includes receiving at least one of an electrical activity level, a galvanic potential, or a skin resistance.

Example 59 includes the subject matter of any of Examples 55-58, and wherein demultiplexing the body area network signals comprises demultiplexing the body the biofeedback signals to produce a biofeedback signal in a low frequency range and a body-coupled communications signal in a high frequency range that is higher than the low frequency range.

Example 60 includes the subject matter of any of Examples 55-59, and wherein the low frequency range is from 1 Hz to 150 Hz and the high frequency range is from 1 MHz to 100 MHz.

Example 61 includes the subject matter of any of Examples 55-60, and wherein processing the biofeedback signal by the sensor signal conditioning circuit comprises processing the biofeedback signal by at least one of a transimpedance amplifier, a variable gain amplifier, or a filter.

Example 62 includes the subject matter of any of Examples 55-61, and further including providing, to an output interface, feedback to a user of the body area network controller based on the output data.

Example 63 includes the subject matter of any of Examples 55-62, and wherein providing the feedback to the user includes providing at least one of a visual feedback, an audible feedback, or a tactile feedback.

Example 64 includes the subject matter of any of Examples 55-63, and further including receiving, by an input interface, an input command from a user of the body area network controller to control one or more of the biofeedback sensors.

Example 65 includes the subject matter of any of Examples 55-64, and wherein receiving the input command comprises receiving at least one of an interrogation command to request a real-time sensor data from one or more of the biofeedback sensors or a calibration command to instruct at least one of the biofeedback sensors to calibrate.

Example 66 includes the subject matter of any of Examples 55-65, and wherein receiving the body area network signals by the body interface comprises receiving the body area network signals by a conductive metallic plate.

Example 67 includes the subject matter of any of Examples 55-66, and wherein receiving the body area network signals by the body interface comprises receiving the body area network signals by a body interface in direct contact with at least one of a body of the user and a conductive medium.

Example 68 includes the subject matter of any of Examples 55-67, and wherein receiving the body area network signals by the body interface comprises receiving the body area network signals by a body interface in indirect contact with the body.

Example 69 includes the subject matter of any of Examples 55-68, and wherein demultiplexing the body area network signals by a signal multiplexer of the biofeedback sensor comprises demultiplexing the body area network signals by a diplexer.

Example 70 includes the subject matter of any of Examples 55-69, and wherein demultiplexing the body area network signals by the signal multiplexer of the biofeedback sensor comprises demultiplexing the body area network signals by at least one of a low pass filter or a high pass filter.

Example 71 includes a biofeedback sensor for sensing biofeedback signals of a user, the biofeedback sensor comprising a processor; and a memory having stored therein a plurality of instructions that when executed by the processor cause the biofeedback sensor to perform the method of any of Examples 41-54.

Example 72 includes one or more machine readable media comprising a plurality of instructions stored thereon that in response to being executed result in a biofeedback sensor performing the method of any of Examples 41-54.

Example 73 includes a body area network controller for controlling a body area network comprising one or more biofeedback sensors, the body area network controller comprising a processor; and a memory having stored therein a plurality of instructions that when executed by the processor cause the body area network controller to perform the method of any of Examples 55-70.

Example 74 includes one or more machine readable media comprising a plurality of instructions stored thereon that in response to being executed result in a body area network controller performing the method of any of Examples 55-70.

Example 75 includes a method for sensing body area network signals of a user, the method comprising means for receiving, by a body interface of a biofeedback sensor, body area network signals of the user; means for demultiplexing, by a signal multiplexer of the biofeedback sensor, the body area network signals to produce a biofeedback signal and a body-coupled communication signal; means for processing, by a sensor signal conditioning circuit of the biofeedback sensor, the biofeedback signal; and means for processing, by a body area network communication circuit, the body-coupled communication signal.

Example 76 includes the subject matter of Example 75, and further including means for transmitting, by the body area network communication circuit, an outgoing body-coupled communication signal; and means for multiplexing, by the signal multiplexer, the outgoing body-coupled communication signal with the biofeedback signal.

Example 77 includes the subject matter of any of Examples 75 and 76, and further including means for generating, by a sensor controller, sensor data based on the biofeedback signal; and means for controlling, by the sensor controller, the body area network communication circuit to transmit the sensor data to a body area network controller by body-coupled communication.

Example 78 includes the subject matter of any of Examples 75-77, and wherein means for generating the sensor data is further based on a unique identifier corresponding to the biofeedback sensor.

Example 79 includes the subject matter of any of Examples 75-78, and wherein means for generating the sensor data based on the biofeedback signal comprises means for generating, by a media access controller, sensor data based on the biofeedback signal.

Example 80 includes the subject matter of any of Examples 75-79, and wherein means for receiving the body area network signals by the body interface comprises means for receiving the body area network signals by a conductive metallic plate.

Example 81 includes the subject matter of any of Examples 75-80, and wherein means for receiving the body area network signals by the body interface comprises means for receiving the body area network signals by a body interface in direct contact with at least one of a body of the user or a conductive medium.

Example 82 includes the subject matter of any of Examples 75-81, and wherein means for receiving the body area network signals by the body interface comprises means for receiving the body area network signals by a body interface in indirect contact with the body.

Example 83 includes the subject matter of any of Examples 75-82, and wherein means for demultiplexing the body area network signals by a signal multiplexer of the biofeedback sensor comprises means for demultiplexing the body area network signals by a diplexer.

Example 84 includes the subject matter of any of Examples 75-83, and wherein means for demultiplexing the body area network signals by the signal multiplexer comprises means for demultiplexing the body area network signals by at least one of a low pass filter or a high pass filter.

Example 85 includes the subject matter of any of Examples 75-84, and wherein means for receiving the body area network signals of the user includes means for receiving at least one of an electrical activity level, a galvanic potential, or a skin resistance.

Example 86 includes the subject matter of any of Examples 75-85, and wherein means for demultiplexing the body area network signals comprises means for demultiplexing the body the biofeedback signals to produce a biofeedback signal in a low frequency range and a body-coupled communications signal in a high frequency range that is higher than the low frequency range.

Example 87 includes the subject matter of any of Examples 75-86, and wherein the low frequency range is from 1 Hz to 150 Hz and the high frequency range is from 1 MHz to 100 MHz.

Example 88 includes the subject matter of any of Examples 75-87, and wherein means for processing the biofeedback signal by the sensor signal conditioning circuit comprises means for processing the biofeedback signal by at least one of a transimpedance amplifier, a variable gain amplifier, or a filter.

Example 89 includes a method for controlling a body area network comprising one or more biofeedback sensors, the method comprising means for receiving, by a body interface of a body area network controller, body area network signals of the user; means for demultiplexing, by a signal multiplexer of the body area network controller, the body area network signals to produce a body-coupled communication signal, the body-coupled communication signal comprising a communication signal transmitted by one of the biofeedback sensors using body-coupled communication; means for processing, by a body area network communication circuit, the communication signal; and means for generating, by a body area network system controller of the body area network controller, output data based on the communication signal.

Example 90 includes the subject matter of Example 89, and further including means for demultiplexing, by the signal multiplexer of the body area network controller, the body area network signals to produce a biofeedback signal; means for processing, by a sensor signal conditioning circuit coupled to the signal multiplexer, the biofeedback signal; and means for generating, by the body area network system controller, sensor data based on the biofeedback signal.

Example 91 includes the subject matter of any of Examples 89 and 90, and further including means for transmitting, by the body area network communication circuit, an outgoing body-coupled communication signal; and means for multiplexing, by the signal multiplexer, the outgoing body-coupled communication signal with the biofeedback signal.

Example 92 includes the subject matter of any of Examples 89-91, and wherein means for receiving the body area network signals of the user includes means for receiving at least one of an electrical activity level, a galvanic potential, or a skin resistance.

Example 93 includes the subject matter of any of Examples 89-92, and wherein means for demultiplexing the body area network signals comprises means for demultiplexing the body the biofeedback signals to produce a biofeedback signal in a low frequency range and a body-coupled communications signal in a high frequency range that is higher than the low frequency range.

Example 94 includes the subject matter of any of Examples 89-93, and wherein the low frequency range is from 1 Hz to 150 Hz and the high frequency range is from 1 MHz to 100 MHz.

Example 95 includes the subject matter of any of Examples 89-94, and wherein means for processing the biofeedback signal by the sensor signal conditioning circuit comprises means for processing the biofeedback signal by at least one of a transimpedance amplifier, a variable gain amplifier, or a filter.

Example 96 includes the subject matter of any of Examples 89-95, and further including means for providing, to an output interface, feedback to a user of the body area network controller based on the output data.

Example 97 includes the subject matter of any of Examples 89-96, and wherein means for providing the feedback to the user includes means for providing at least one of a visual feedback, an audible feedback, or a tactile feedback.

Example 98 includes the subject matter of any of Examples 89-97, and further including means for receiving, by an input interface, an input command from a user of the body area network controller to control one or more of the biofeedback sensors.

Example 99 includes the subject matter of any of Examples 89-98, and wherein means for receiving the input command comprises means for receiving at least one of an interrogation command to request a real-time sensor data from one or more of the biofeedback sensors or a calibration command to instruct at least one of the biofeedback sensors to calibrate.

Example 100 includes the subject matter of any of Examples 89-99, and wherein means for receiving the body area network signals by the body interface comprises means for receiving the body area network signals by a conductive metallic plate.

Example 101 includes the subject matter of any of Examples 89-100, and wherein means for receiving the body area network signals by the body interface comprises means for receiving the body area network signals by a body interface in direct contact with at least one of a body of the user and a conductive medium.

Example 102 includes the subject matter of any of Examples 89-101, and wherein means for receiving the body area network signals by the body interface comprises means for receiving the body area network signals by a body interface in indirect contact with the body.

Example 103 includes the subject matter of any of Examples 89-102, and wherein means for demultiplexing the body area network signals by a signal multiplexer of the biofeedback sensor comprises means for demultiplexing the body area network signals by a diplexer.

Example 104 includes the subject matter of any of Examples 89-103, and wherein means for demultiplexing the body area network signals by the signal multiplexer of the biofeedback sensor comprises means for demultiplexing the body area network signals by at least one of a low pass filter or a high pass filter.

The invention claimed is:

1. A biofeedback sensor for sensing biofeedback signals of a user, the biofeedback sensor comprising:
    a body interface wearable by the user to receive body area network signals;
    a signal multiplexer having an input coupled to the body interface of the biofeedback sensor to receive the body area network signals, a first output, and a second output, the signal multiplexer to demultiplex the body area network signals to produce one or more biofeedback signals at the first output and a body-coupled communication signal at the second output; and
    a plurality of sensor signal conditioning circuits coupled to the first output of the signal multiplexer, each of the plurality of sensor signal conditioning circuits to process a different type of biofeedback signal; and
    a body area network communication circuit coupled to the second output of the signal multiplexer, the body area network communication circuit to:
        determine whether the body-coupled communication signal is transmitted from a body-area network controller via the body of the user;
        process the body-coupled communication signal in response to a determination that the body-coupled communication signal is from the body-area network controller;
        determine whether the body-coupled communication signal includes a request for the biofeedback sensor from the body-area network controller to adjust the processing of the biofeedback signal; and
        control the plurality of sensor signal conditioning circuits, in response to a determination that the body-coupled communication signal includes the request for the biofeedback sensor to adjust the processing of the biofeedback signal, to select at least one of the plurality of sensor signal conditioning circuits to monitor and process a different type of biofeedback signal of the body area network signals different from a present type of biofeedback signal presently monitored by the biofeedback sensor.

2. The biofeedback sensor of claim 1, wherein:
    the body area network communication circuit is further to transmit an outgoing body-coupled communication signal, and
    the signal multiplexer comprises a bi-directional signal multiplexer to multiplex the outgoing body-coupled communication signal with the biofeedback signal.

3. The biofeedback sensor of claim 1, further comprising a sensor controller to generate sensor data based on the biofeedback signal and control the body area network communication circuit to transmit the sensor data to a body area network controller via body-coupled communication.

4. The biofeedback sensor of claim 1, wherein the body interface of the biofeedback sensor is in direct contact with at least one of a body of the user or a conductive medium.

5. The biofeedback sensor of claim 1, wherein the signal multiplexer includes at least one of a diplexer, a low pass filter, and a high pass filter.

6. The biofeedback sensor of claim 1, wherein the biofeedback signal comprises at least one of an electrical activity level, a galvanic potential, or a skin resistance.

7. The biofeedback sensor of claim 1, wherein the biofeedback signal is in a low frequency range and the body-coupled communication signal is in a high frequency range that is higher than the low frequency range.

8. The biofeedback sensor of claim 7, wherein the high frequency range comprises frequencies greater than one megahertz.

9. The biofeedback sensor of claim 7, wherein the high frequency range comprises frequencies greater than ten megahertz.

10. The biofeedback sensor of claim 1, wherein the signal multiplexer is further to produce a second body-coupled communication signal at the second output, and where the body area network communication circuit is further to:
- determine whether the second body-coupled communication signal is from a body-area network controller; and
- ignore the second body-coupled communication signal in response to a determination that the second body-coupled communication signal is not from the body-area network controller.

11. The biofeedback sensor of claim 1, wherein the body-coupled communication signal comprises a signal to transmit an aggregated chunk of sensor data, and wherein to process the body-coupled communication signal comprises to:
- determine whether the body-coupled communication signal is from a body-area network controller; and
- send, in response to a determination that the body-coupled communication signal is from the body-area network controller, the aggregated chunk of sensor data to the body-area network controller.

12. One or more non-transitory machine-readable storage media comprising a plurality of instructions stored thereon that, in response to being executed cause a biofeedback sensor to:
- receive, by a body interface worn by the a user of the biofeedback sensor, body area network signals of the user;
- demultiplex, by a signal multiplexer of the biofeedback sensor, the body area network signals to produce one or more biofeedback signals and a body-coupled communication signal;
- process, by a plurality of sensor signal conditioning circuits of the biofeedback sensor, the one or more biofeedback signals, each of the plurality of sensor signal conditioning circuits to process a different type of biofeedback signal;
- determine whether the body-coupled communication signal is transmitted from a body-area network controller via the body of the user;
- process, by a body area network communication circuit, the body-coupled communication signal in response to a determination that the body-coupled communication signal is from the body-area network controller;
- determine whether the body-coupled communication signal includes a request for the biofeedback sensor from the body-area network controller to adjust the processing of the biofeedback signal; and
- control the plurality of sensor signal conditioning circuits, in response to a determination that the body-coupled communication signal includes the request for the biofeedback sensor to adjust the processing of the biofeedback signal, to select at least one of the plurality of sensor signal conditioning circuits to monitor and process a different type of the biofeedback signal of the body area network signals different from a present type of biofeedback signal presently monitored by the biofeedback sensor.

13. The one or more non-transitory machine-readable storage media of claim 12, wherein the plurality of instructions further cause the biofeedback sensor to:
- transmit, by the body area network communication circuit, an outgoing body-coupled communication signal; and
- multiplex, by the signal multiplexer, the outgoing body-coupled communication signal with the biofeedback signal.

14. The one or more non-transitory machine-readable storage media of claim 12, wherein the plurality of instructions further cause the biofeedback sensor to:
- generate, by a sensor controller, sensor data based on the biofeedback signal; and
- control, by the sensor controller, the body area network communication circuit to transmit the sensor data to a body area network controller by body-coupled communication.

15. The one or more non-transitory machine-readable storage media of claim 12, wherein to demultiplex the body area network signals by the signal multiplexer comprises to demultiplex the body area network signals by at least one of a diplexer, a low pass filter, or a high pass filter.

16. The one or more non-transitory machine-readable storage media of claim 12, wherein to demultiplex the body area network signals comprises to demultiplex the body the biofeedback signals to produce a biofeedback signal in a low frequency range and a body-coupled communications signal in a high frequency range that is higher than the low frequency range.

* * * * *